United States Patent
Stapf et al.

(10) Patent No.: US 6,323,386 B1
(45) Date of Patent: Nov. 27, 2001

(54) WOUND COVERING FOR A FOOT OR HAND

(75) Inventors: Donald Stapf, Minneapolis; Scott D. Augustine, Bloomington; Keith J. Leland, Plymouth, all of MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

(21) Appl. No.: 09/437,388

(22) Filed: Nov. 10, 1999

(51) Int. Cl.$^7$ .................................................... A61F 13/00
(52) U.S. Cl. ................................... 602/41; 602/2; 602/42
(58) Field of Search .............................. D24/190; 602/3, 602/41–59; 607/96, 108, 111, 112, 113, 114

(56) References Cited

U.S. PATENT DOCUMENTS

| | | | | |
|---|---|---|---|---|
| 4,178,924 | * | 12/1979 | Baxter | 602/3 |
| 5,407,419 | * | 4/1995 | Kelly et al. | 602/3 |
| 5,605,534 | * | 2/1997 | Hutchison | 602/3 |

* cited by examiner

Primary Examiner—Kim M. Lewis
(74) Attorney, Agent, or Firm—Gray Cary Ware & Freidenrich

(57) ABSTRACT

A non-contact wound treatment device suitable for use on an extremity, such as a hand or foot, includes a wound cover formed as a bag, sac, or pouch, and a support member disposable within the wound cover to support a portion of the wound cover off of, and out of contact with, a wound. The wound cover has an open end with attachment means disposed thereon for attachment to a limb whose extremity is received in the wound cover.

13 Claims, 4 Drawing Sheets

WOUND COVERING FOR A FOOT OR HAND

FIELD OF THE INVENTION

The invention described herein relates to a wound treatment device, and in particular, to a wound treatment device configured so as to provide a wound cover out of contact with a wound on an awkwardly shaped body part, such as a foot, or a hand, that is capable of delivering heat to the wound.

BACKGROUND OF THE INVENTION

A novel mode of wound treatment employing a non-contact wound treatment device is disclosed in detail in published PCT applications WO 94/00090, WO 96/1574455 and WO 98/46179, each of which is owned in common with the present application. The device covers a wound, forming a treatment volume above and over the wound. The device is comprised of a plurality of parts, principally an attachment portion, a wound treatment portion, and a transition portion, each having a specific function.

The attachment portion connects and retains the wound treatment device on the skin of a patient. The wound treatment portion generally comprises a standoff that rises above the patient's skin surface and a wound cover that spans the open portion of the standoff. Together the standoff and wound cover define a wound treatment volume. The transition portion connects the attachment portion to the wound treatment portion.

One of the important functions of the transition portion is to adapt the wound treatment device to the contours of the part of the patient's body to which the device is attached and to accommodate movements of the patient that deform the attached wound treatment device. This is particularly challenging when the wound is located on a portion of the body having a relatively low surface area or a tightly curved shape, such as a foot or hand. Substantial stress is put on the attached wound treatment device resulting in deformation of the device, detachment from the skin, and the like. A need exists, therefore, for a wound treatment device with improved performance characteristics when used on body parts such as hands and feet. The present invention addresses that need.

SUMMARY OF THE INVENTION

The present invention is a wound treatment device that is particularly well suited to treating wounds on the hand or foot of a patient. Wounds, as used herein, are breaks in the integrity of the skin, either caused mechanically (cuts, burns, and the like) or by reduction in vascular perfusion. Reduced vascular perfusion can cause secondary weakening of the tissues, which eventually disrupt and cause an ulcerated wound. Such wounds commonly occur on a patient's extremities, and are particularly difficult to treat.

The invention is a non-contact wound treatment device having a wound cover formed as a bag, sac, or pouch, one or more flexible attachment portions, and a support member supporting a portion of the wound cover off of and out of contact with a wound. The wound cover has an end and an end edge. The one or more attachment portions are disposed at the end edge of the wound cover.

The support member, which supports the wound cover, can comprise a ring made of, for example, a foam material. In an alternative embodiment, the support member can comprise a generally rectangular member having a central cutout and comprising two side extensions and one end extension which can be folded around the hand or foot undergoing treatment.

BRIEF DESCRIPTION OF THE DRAWINGS

The various figures depict illustrative and exemplary forms of the wound treatment device disclosed herein. Throughout the several views, identical reference numbers represent similar or equivalent structures.

DETAILED DESCRIPTION

Figure 1:
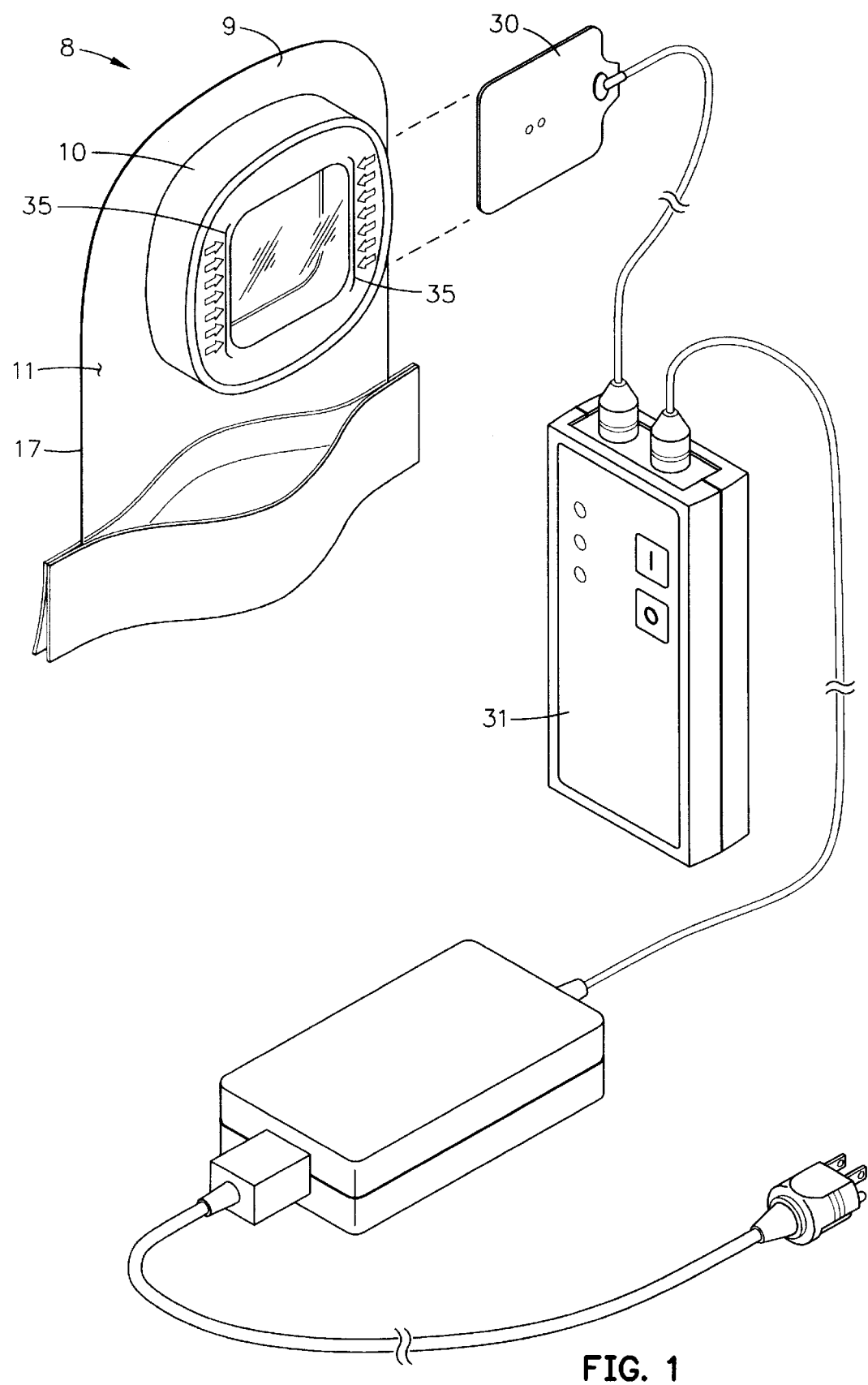
FIG. 1 is a perspective view of one embodiment of the wound treatment device in combination with a heating system.

Reference is made to FIGS. 1–4 in which embodiments and elements of the present wound treatment device are illustrated. With respect to FIGS. 1 and 2, there is shown a wound treatment device 8 that includes a wound cover 9 formed as a bag, sac, or pouch, and a support member 10 with an open end. In this description, the wound cover is constructed from two sheets of material; this construction is merely for illustration and is not intended to so limit the construction of the cover 9. In this construction, the wound cover 9 includes a first sheet 11 and a second sheet 12, each of approximately the same size and shape. The first sheet 11 has an edge 13 and an end 14. The second sheet 12 likewise has an edge 15 and an end 16. A continuous seal 17 is formed between the first and the second edges 13 and 15, joining the two sheets 11 and 12. Together the joined sheets form an enclosure that can fit over an extremity. The enclosure has an open end 14, 16 through which the extremity can extend. Alternatively, the wound cover 9 may be made from a single sheet of flexible material, or formed as a single member.

Preferably the material of which the wound cover 9 is made is a flexible, easily worked material that is adaptable to automated manufacturing. Such synthetic materials as flexible plastics are examples. Other materials such as woven and non-woven synthetics, natural, or blended materials are contemplated. The chosen material may be clear or opaque.

Figure 2:
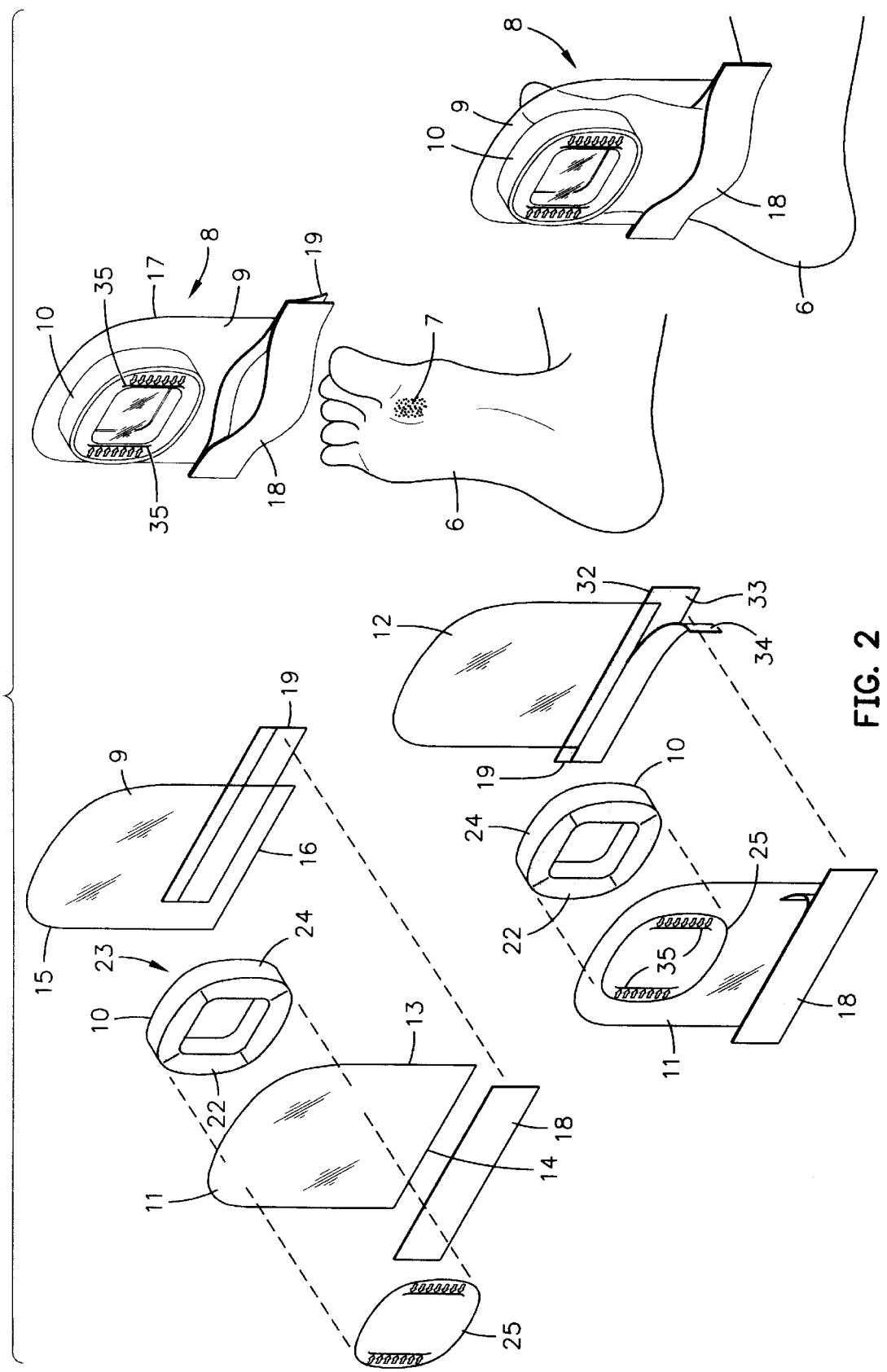
FIG. 2 is an exploded view of one embodiment of the wound treatment device showing an exemplary construction.
Figure 4:
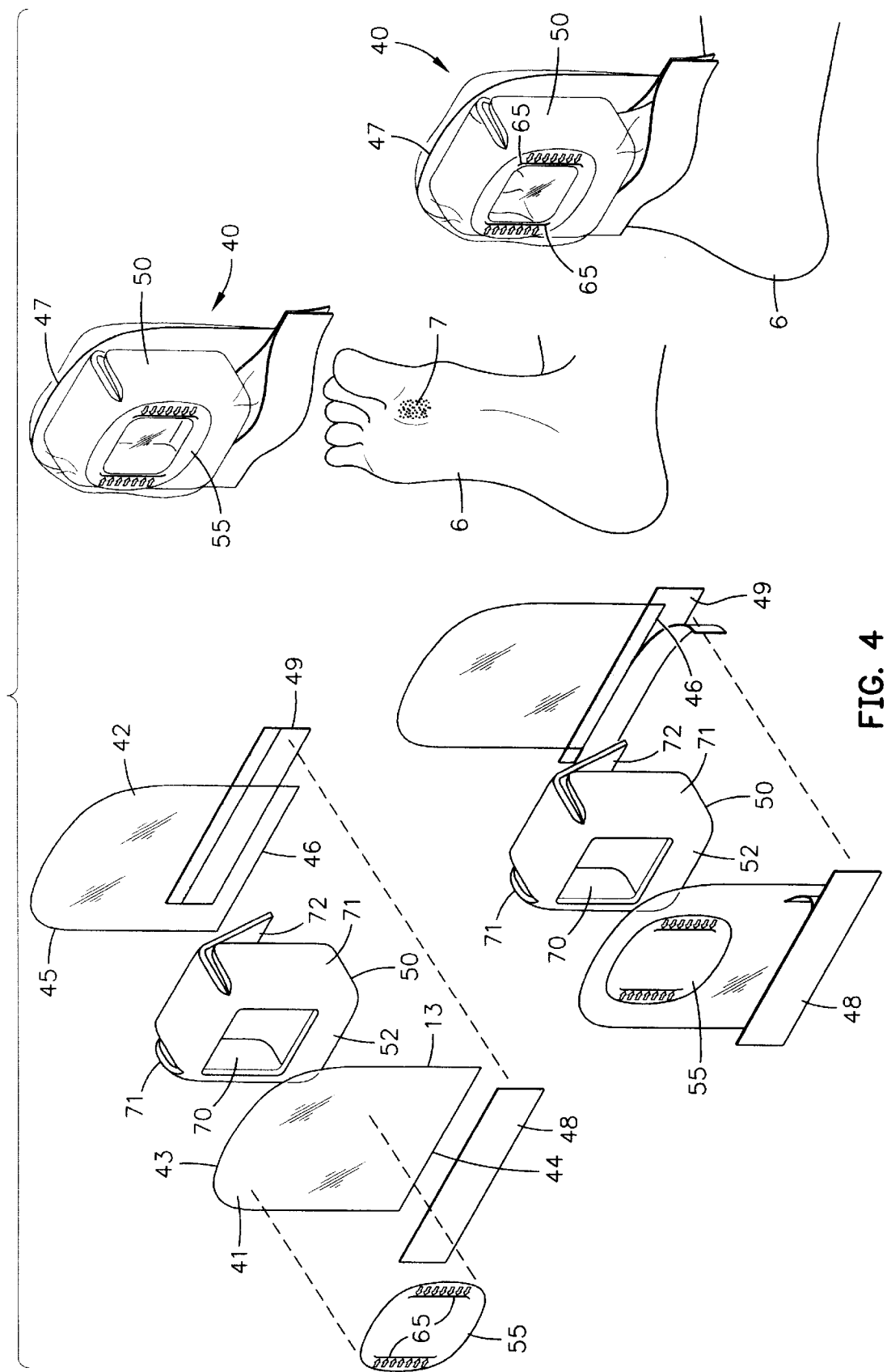
FIG. 4 is an exploded view of an alternative embodiment of the wound treatment device.
Figure 2:
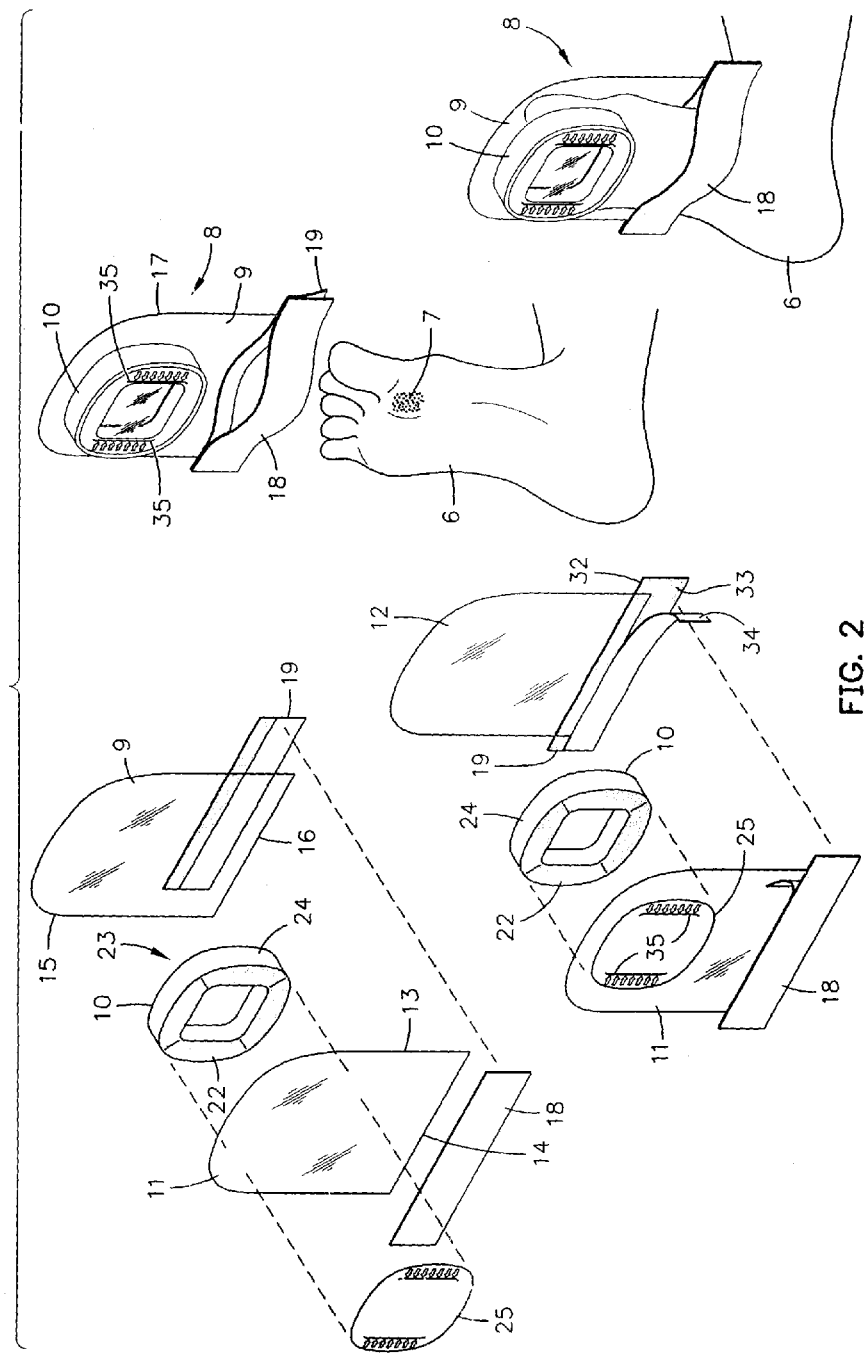

The wound treatment device further comprises attachment portions 18, 19, which are disposed along the end 14, 16. The attachment portions are used to connect the wound treatment device 8 to the skin of a patient, sealing the enclosure formed by the wound cover 9 to a patient's extremity as illustrated in FIG. 2. In FIGS. 2 and 4, the extremity is a foot 6 on the bottom of which is a wound 7.

Referring now to FIG. 2, in the wound treatment device 10, the attachment portions 18, 19 are integrated unitary assemblies, each preferably having three sections: a foam layer 32, an adhesive film layer 33 on a bottom surface of the foam layer 32, and a release liner 34 covering the adhesive film layer 33. One or more lines of weakness or perforation are provided on the release liner 34 so that its parts may be separated and selectably peeled off of the adhesive film layer 33, thereby exposing the adhesive film layer for attaching to a patient's skin. The foam layer 32 may comprise a naturally open-celled polyurethane foam, and is preferably approximately 1/16" thick. The adhesive film layer 33 may comprise a high MVTR thin film pressure sensitive adhesive (PSA) laminate available as a package under the trade name Mediderm from Bertek. The foam layer 32 is heat bonded to the adhesive film layer 33. The material of which the adhesive film layer is comprised is selected for a combination of adhesion level, permeability, and conformability (stretching and flexing with the skin) to allow prolonged skin contact without complications. The release liner 34 is a white release paper coated with a release agent that is provided on the Mediderm 3701 product. The perforations or slits are made during assembly to aid in the removal of the release liner 34 prior to attachment of a wound treatment device 10 to a person.

The wound treatment device 8 disclosed herein further comprises a support member 10 for supporting a portion of the upper wound cover 8 off of or away from a wound so as to prevent the wound cover portion from contacting the wound (or at least to minimize such contact). In one embodiment, illustrated in FIGS. 1 and 2, the support member is in the shape of a ring. The ring-shaped support member 10 has a first surface 22, a second surface 23 (not visible in the figures), and an outer perimeter or edge 24. A portion of the inner surface of the wound cover 9 is attached to the first surface 22 of the support member 10 as described below. The wound cover 9 is preferably sized to extend beyond the outer perimeter 24 of the support member 10 as illustrated in FIGS. 1 and 2.

The ring-shaped support member 10 is preferably comprised of foam material, most preferably an absorbent foam. An example of a suitable absorbent foam is a naturally open-celled polyurethane foam that is selected to have favorable characteristics of liquid absorbency, leaking, and resevoiring. Such material is a super absorbent polymer (SAP) filled from, which may be obtained from Neosorb, Woodbridge, MD. An alternative is available as a product sold under the trade name Aquazone from Foamex. The thickness of the ring-shaped support member 10 is preferably in a range extending from 3/8" to 5/8", with the exact dimension being selected to maintain the wound cover off of a wound site such as on the foot 6 whereby, during use, the foam ring 10 can compress and conform without the wound cover 9 contacting the wound 7.

The second surface 23 of the ring-shaped support member 10 may optionally have a moisture barrier film adhered thereto. Such a moisture barrier film allows for smooth contact between the support member 10 and the patient's skin and may prevent maceration of the skin if the support member 10 is wetted by soaking up wound exudate. Optimally, the film would be porous or perforated to allow exudate to be wicked away from the skin and trapped in the foam material of the support member 10. Any moisture barrier film would be suitable, in particular those composed of polyurethane, polyethylene, and the like. The film may be attached to the second surface 23 by means of heat sealing or a ring of adhesive, such as the product sold under the trade name HL-2306-X by H. B. Fuller Adhesive.

The material of the wound cover 9 preferably is a 2 mil.-thick clear flexible polyurethane film with favorable characteristics selected, but not limited, to include moisture vapor transfer (MVTR), oxygen permeability, and transmission of infrared radiation. A measurable MVTR is particularly desirable when the wound treatment apparatus is deployed over hands and feet, which sweat profusely. Such material is available sold under the trade name Deerfield 6100S. The portion of the inner surface of the wound cover 9 is attached to the upper surface 22 of the support member 10 by a ring of adhesive comprising a synthetic rubber-base adhesive, such as the product sold under the trade name HL-2306-X.

A stretcher layer 25 may be attached to the outer surface of the wound cover 9 against the support member 10 such that the wound cover is sandwiched between the stretcher layer 25 and the first surface 22 of the support member 10. The stretcher layer 25 is a 3 mil-thick planar sheet of (preferably) clear, somewhat flexible polyester film having enough stiffness to aid in maintaining planarity. The function of the stretcher layer 25 is to hold the portion of the wound cover 9 under it taut, much as a "stretcher frame" tautens an artist's canvas. The stretcher layer 25 is attached to the wound cover 9 by a layer of adhesive comprising a clear flexible polyester carrier film coated on both sides with an aggressive adhesive. The adhesive layer is oriented over the first surface 22 of the support member 20. The stretcher layer 25 further includes a pair of slits 35 that receive a detachable heater 30. With the provision of the slits 35, a pocket is formed between the stretcher layer 25 and the wound cover 9.

FIG. 1 shows a detachable heater 30 positioned to slide into a slit 35 in the stretcher layer 25 which forms a pocket with the wound cover 9. When inserted, the heater 30 is supported substantially in a plane or surface above a wound by the support member 10. The heater 30 is generally planar and may be connected to and powered by a portable power supply 31, such as those heaters described in detail in published PCT applications WO 98/831309 and WO 98/831310, each of which is owned in common with the present application. The application of heat may be of particular therapeutic benefit by improving cellular physiologic functions, immune competence, and perfusion in the wound area.

Figure 3:
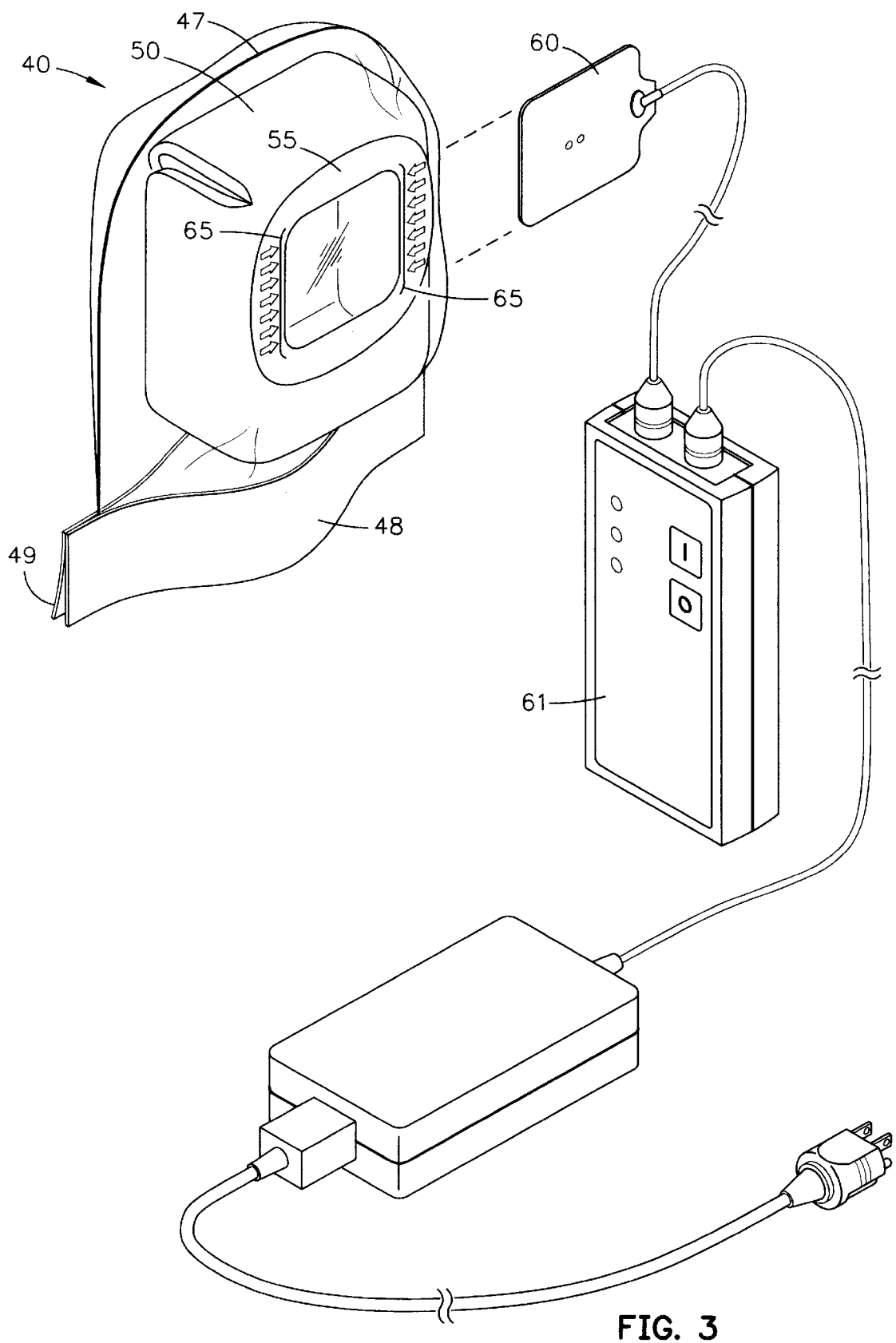
FIG. 3 is a perspective view of an alternative embodiment of the wound treatment device in combination with a heating system.

An alternative embodiment of the present invention is illustrated in FIGS. 3 and 4. FIG. 4 shows an exploded view of a non-contact wound treatment device 40 for use on an extremity having a wound cover 45 that is a bag, sac, or pouch made in any of the ways with any of the materials described above in connection with the wound cover 9. For illustration and by way of example only, the wound cover 45 is shown in FIG. 4 as being made from two sheets.

The wound treatment device of FIG. 4 further comprises a support member 50, which is generally rectangular and has a central cutout 70, two side extensions 71, and an end extension 72. The support member 50 is made of a flexible foam material, such as that used for the support member 10 described above in a thickness ranging from 1/4" to 5/8". A thinner foam is preferred for increased conformability. The side 71 and end 72 extensions are flexible and can be folded so that they enclose the extremity under treatment, as illustrated in FIG. 4. The inner surface of the support member 50 may optionally be all or partially modified by having a moisture barrier film adhered thereto, as described for the ring-shaped support member 10 above.

The support member furthermore has a first surface 52 to which a portion of the inner surface of the wound cover 45 is attached generally in the same manner and using similar materials as described above.

Attached to the outer surface of the wound cover 45, above the support member 50, is a stretcher layer 55 such that a portion of the wound cover is sandwiched between the stretcher layer 55 and the first surface 52 of the support member 50. The stretcher layer 55 has approximately the same function as the stretcher layer 25, described above, and is generally composed of and attached in the same manner and using similar materials as described above. The stretcher layer 55 further includes a pair of slits 65 that receive a detachable heater 60. With the provision of the slits 65, a pocket is formed between the stretcher layer 55 and the first wound cover 41.

FIG. 3 shows the detachable heater 60 positioned to slide into a slit 65 in the stretcher layer 55 which forms a pocket with first wound cover 41. When inserted, the heater 60 is supported substantially in a plane or surface above a wound by the support member 50. The heater 60 is generally planar and may be connected to and powered by a portable power supply 61.

While the invention has been illustrated by means of specific embodiments and examples of use, it will be evident to those skilled in the art that many variations and modifications may be made therein without deviating from the scope and spirit of the invention. However, it is to be understood that the scope of the present invention is to be limited only by the appended claims.

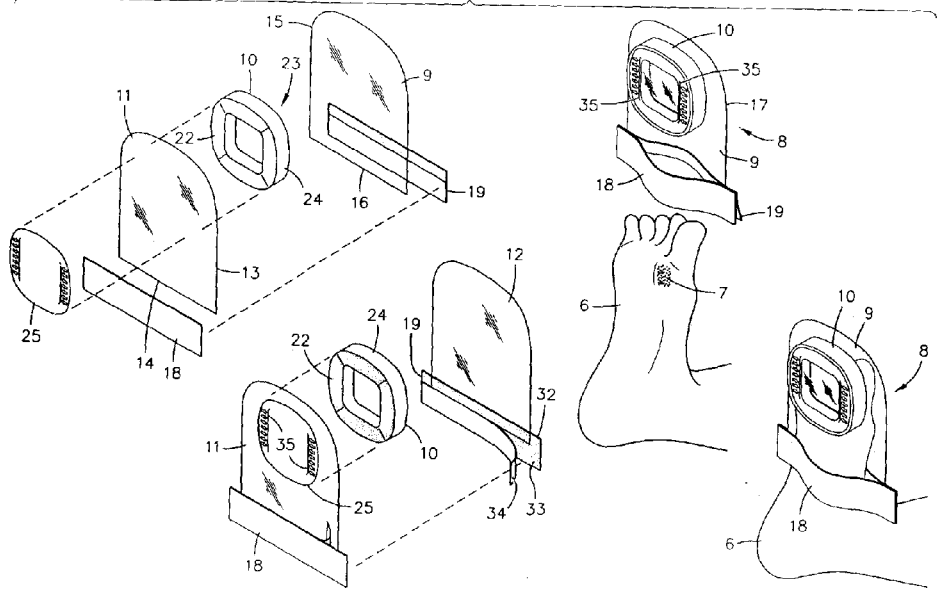

We claim:

1. A non-contact wound treatment device, comprising:
   a bag-like wound cover with an open end;
   one or more attachment portions disposed along the open end; and
   a generally rectangular support member for disposal within the wound cover, the generally rectangular support member having a central cutout and comprising two side extensions and one end extension.

2. The non-contact wound treatment device of claim 1, wherein said rectangular member comprises a foam material.

3. The non-contact wound treatment device of claim 2, wherein said foam material is absorbent foam.

4. The non-contact wound treatment device of claim 1, wherein said wound cover further includes an outer surface, the wound treatment device further including a planar layer of flexible material joined to said outer surface.

5. The non-contact wound treatment device of claim 4, wherein the planar layer comprises at least one slit, said slit opening into a pocket formed by said planar layer and said wound cover.

6. The non-contact wound treatment device of claim 5, further comprising a heater disposed in said pocket.

7. The non-contact wound treatment device of claim 6, further comprising a power supply connected to said heater.

8. The non-contact wound treatment device of claim 1, wherein said one or more attachment portions each comprises a layer of foam material.

9. The non-contact wound treatment device of claim 8, wherein each attachment portion further comprises adhesive material carried on a surface of said layer of foam material and a release layer carried on said adhesive material.

10. The non-contact wound treatment device of claim 9, wherein said release layer has one or more lines of weakness for permitting a portion of the release layer to be removed from the adhesive material.

11. The non-contact wound treatment device of claim 10, wherein said layer of foam material comprises open-cell foam material.

12. The non-contact wound treatment device of claim 1, wherein said wound cover comprises two opposing sheets joined along respective opposing edges.

13. The non-contact wound treatment device of claim 12, each sheet comprising a 2 mil. thick film of polyurethane.

* * * * *

UNITED STATES PATENT AND TRADEMARK OFFICE
CERTIFICATE OF CORRECTION

PATENT NO.   : 6,323,386 B1
DATED        : November 27, 2001
INVENTOR(S)  : Donald Staph et al.

It is certified that error appears in the above-identified patent and that said Letters Patent is hereby corrected as shown below:

Title page,
The title page showing the illustrative figure should be deleted and replaced with the attached title page.

Drawings,
Sheet 2 of 4, consisting of Figure 2, should be deleted and replace with the corrected Figure 2, as shown on the attached page.

Signed and Sealed this

Twenty-fifth Day of June, 2002

Attest:

Attesting Officer

JAMES E. ROGAN
Director of the United States Patent and Trademark Office

(12) United States Patent
Stapf et al.

(10) Patent No.: US 6,323,386 B1
(45) Date of Patent: Nov. 27, 2001

(54) WOUND COVERING FOR A FOOT OR HAND

(75) Inventors: Donald Stapf, Minneapolis; Scott D. Augustine, Bloomington; Keith J. Leland, Plymouth, all of MN (US)

(73) Assignee: Augustine Medical, Inc., Eden Prairie, MN (US)

(*) Notice: Subject to any disclaimer, the term of this patent is extended or adjusted under 35 U.S.C. 154(b) by 0 days.

(21) Appl. No.: 09/437,388

(22) Filed: Nov. 10, 1999

(51) Int. Cl.$^7$ .................................................... A61F 13/00
(52) U.S. Cl. .................................. 602/41; 602/2; 602/42
(58) Field of Search .......................... D24/190; 602/3, 602/41–59; 607/96, 108, 111, 112, 113, 114

(56) References Cited

U.S. PATENT DOCUMENTS

| | | | |
|---|---|---|---|
| 4,178,924 | * | 12/1979 | Baxter ................................ 602/3 |
| 5,407,419 | * | 4/1995 | Kelly et al. ........................ 602/3 |
| 5,605,534 | * | 2/1997 | Hutchison .......................... 602/3 |

* cited by examiner

*Primary Examiner*—Kim M. Lewis
(74) *Attorney, Agent, or Firm*—Gray Cary Ware & Freidenrich

(57) ABSTRACT

A non-contact wound treatment device suitable for use on an extremity, such as a hand or foot, includes a wound cover formed as a bag, sac, or pouch, and a support member disposable within the wound cover to support a portion of the wound cover off of, and out of contact with, a wound. The wound cover has an open end with attachment means disposed thereon for attachment to a limb whose extremity is received in the wound cover.

13 Claims, 4 Drawing Sheets